United States Patent
Park

(10) Patent No.: US 8,623,845 B1
(45) Date of Patent: Jan. 7, 2014

(54) **PHARMACEUTICAL COMPOSITION FOR PREVENTING OR TREATING *DIABETES MELLITUS* COMPRISING BISPHOPHONATES**

(71) Applicant: Metacine, Inc., Wonju (KR)

(72) Inventor: Bae Keun Park, Wonju (KR)

(73) Assignee: Metacine, Inc., Wonju-si (KR)

( * ) Notice: Subject to any disclaimer, the term of this patent is extended or adjusted under 35 U.S.C. 154(b) by 0 days.

(21) Appl. No.: 13/665,011

(22) Filed: Oct. 31, 2012

(30) Foreign Application Priority Data

Oct. 9, 2012 (KR) .......................... 10-2012-0112030

(51) Int. Cl.
*A01N 57/00* (2006.01)
*A61K 31/675* (2006.01)

(52) U.S. Cl.
USPC ............................................................ 514/94

(58) Field of Classification Search
USPC ............................................................ 514/94
See application file for complete search history.

(56) References Cited

FOREIGN PATENT DOCUMENTS

WO 2006/050843 A1 5/2006

OTHER PUBLICATIONS

Skorey, Kathryn et al., "How Does Alendronate Inhibit Protein-tyrosine Phosphatases?" The Journal of Biological Chemistry, Sep. 5, 1997; pp. 22472-22480; vol. 272, No. 36; The American Society for Biochemistry and Molecular Biology, Inc.; U.S.A.
Qu, Chang-Qing et al., "Osteogenic and adipogenic potential of porcine adipose mesenchymal stem cells"; In Vitro Cell.Dev.Biol.—Animal, 2007, 43:95, pp. 95-100.

*Primary Examiner* — San-Ming Hui
*Assistant Examiner* — Kathrien Cruz
(74) *Attorney, Agent, or Firm* — Novick, Kim & Lee, PLLC; Jae Youn Kim

(57) ABSTRACT

The present invention relates to a pharmaceutical composition comprising a bisphosphonate or a pharmaceutically acceptable salt thereof for preventing or treating diabetes mellitus and a method of preventing or treating diabetes mellitus comprising single or multiple administration of the pharmaceutical composition to a patient in need thereof.

6 Claims, 3 Drawing Sheets

PHARMACEUTICAL COMPOSITION FOR PREVENTING OR TREATING *DIABETES MELLITUS* COMPRISING BISPHOPHONATES

CROSS-REFERENCES TO RELATED APPLICATION

This patent application claims the benefit of priority from Korean Patent Application No. 10-2012-0112030 filed on, Oct. 9, 2012, the contents of which are incorporated herein by reference.

BACKGROUND OF THE INVENTION

1. Field of the Invention

The present invention relates to a pharmaceutical composition comprising a bisphosphonate or a pharmaceutically acceptable salt thereof for preventing or treating diabetes mellitus (more specifically, type II diabetes) and a method comprising single or multiple administration of the pharmaceutical composition to a patient for preventing or treating diabetes mellitus.

2. Description of the Related Art

Bisphosphonates are used widely to inhibit the activity of osteoclasts accompanying excessive or inappropriate bone resorption when treating various benign or malignant diseases. The bisphosphonates, so called pyrophosphate analogs because they are similar in structure to pyrophosphate, reduce the incidence of skeletal related problems (skeletal related events), provide a clinical benefit to patients, and improve survival rate of patients. It has been reported that the bisphosphonates may prevent bone resorption in vivo, and treat osteoporosis, osteopenia, Paget's disease, tumor-induced hypercalcemia (TIH), bone metastasis and multiple myeloma (MM) (reference: Fleisch H 1997 Bisphosphonates clinical. Bisphosphonates in Bone Disease. From the Laboratory to the Patient. Eds: The Parthenon Publishing Group, N.Y./London, pages 68-163). It is identified that the bone resorption inhibition mechanism of bisphosphonates is based on the bisphosphonates' strong coupling with hydroxyapatite crystal of bones, reduction of bone metabolic circulation, reduction of blood hydroxyproline or alkaline phosphatase levels, and inhibition of osteoclasts' formation, supplementation, and activation.

The only commercially used-medicine for bone disease (bone metastasis of breast cancer and osteoporosis) is zoledronic acid of Novartis [Zomera, Aclasta or Reclast]. The zoledronic acid is a chemical of bisphosphonates group, a transformed form of pyrophosphate which was used to prevent corrosion of metal pipes etc.

Pharmacokinetically, while the pyrophosphates having a P—OP structure can be easily hydrolyzed, the bisphosphonates having a P—C—P structure cannot be easily hydrolyzed and thus it has relatively a long-term half-life. The bisphosphonates is used as a treatment for osteoporosis since it reduces bone resorption by inhibiting osteoclasts. Out of the two lateral chains ($R^1$ and $R^2$) binding to carbon atom of bisphosphonates, $R^1$ can bind to calcium of bones with its hydroxide(—OH) group while modifying $R^2$ into various forms to increase the inhibition effect of bone resorptions. Most of the bisphosphonates are structurally highly hydrophilic and the absorption rate is very low and thus they are manufactured to use as an intravenous injection dosage form. The bisphosphonates inhibit the maturation of osteoclasts and prevent bone resorption by attaching to the bone surface of bone formation is actively made. Also, the bisphosphonates inhibit the transferring of osteoclasts to the region of bone resorption and reduce the generation of cytokines stimulating the bone resorption. Beside the actions above, the bisphosphonates prevent the invasion of tumor cells and induce the apoptosis of tumor cells in the bone matrix.

The biggest emerging problem of the bisphosphonates side effects, except the known problems of stroke and atrial fibrillation, is bisphosphonates induced osteonecrosis of the jaws (BIONJ), and the exact mechanism of BIONJ is still unknown. BIONJ is a severe bone disease that affects the maxilla, the mandible and the tooth root and the definitive symptom is the exposure of mandibular or maxillary bone. In healthy bone tissues, a homeostasis is maintained by repetitive bone resorption and bone apposition. Diseased or damaged bone is resorbed through the osteoclasts mediated process and then osteoblasts form new bone to replace it, thus maintaining healthy bone density. This process is commonly called remodeling. The main pharmacological action of bisphosphonates is inhibition of the maturation of osteoclast driven bone resorption, and thus bone resorption is inhibited by bisphosphonates. The bisphosphonates prevent osteoblasts bone formation and thus bone generation is not occurred, and thereby micro-damage and fractures are cumulated. Bisphosphonates may affect to the mucous membrane of the gingiva and the tooth root to be exposed outside of the gingiva. Especially in case of frequently masticated jaw bone, the bone turnover rate of jaw is about 10 times higher than the one of normal bone, and thus it is easily affected by bisphosphonates. Also, the bisphosphonates increases the possibility of occurrence of BIONJ by blocking a sufficient blood supply through the inhibition of blood vessels by bisphosphonates.

Diabetes mellitus, or simply diabetes, is a group of metabolic diseases in which a person has high blood sugar, either because the body does not produce enough insulin, or because cells do not respond to the insulin that is produced. Type II diabetes mellitus results from a deficiency of insulin releasing from pancreas beta cells or combined with insulin resistance, a condition in which cells fail to use insulin properly. In former case, the diabetes mellitus is caused by imbalance between blood glucose homeostasis and lipid/protein metabolism due to the inhibition of phosphorylation of insulin receptor (IR). That is, if the insulin binding with IR is inhibited or dephosphorylation is induced in phosphorylation pathway, then the insulin function may be reduced.

In case of insulin resistance, cells do not respond effectively to the insulin produced by pancreas and thus insulin may be overproduced. It may progress to the state of insulin resistance and the pancreas cannot produce the amount of insulin properly, and finally blood glucose levels will rise.

PTP-1B (protein tyrosine phosphatase 1B) can block the signal transduction of insulin by stimulating dephosphorylation of IR and insulin receptor substrate (IRS). PTP-1B can control insulin sensitivity in liver and perform a unique role in insulin receptor—substrates (i.e., IRS1 and IRS2) interaction and hepatic insulin action mechanism. Recently several PTP-1B inhibitors (i.e., negative regulator of insulin signaling) suggested a treating way of type II diabetes mellitus by increasing insulin sensitivity, improving glucose tolerance and insulin function through maintaining IR phosphorylation state in clinical and non-clinical trials.

CONTENTS OF THE INVENTION

[Tasks to be Accomplished]

The inventor newly identified that the bisphosphonates has anti-diabetes mellitus activities by finding activities of that the zoledronic acid, a bisphosphonates, inhibits the binding of protein tyrosin phosphatase 1B (PTP-1B) with insulin receptor (IR) and improves insulin secretion from pancreas cells.

The present invention is to provide a pharmaceutical composition comprising bisphosphonate or pharmaceutically acceptable salts thereof as an active ingredient for preventing or treating diabetes mellitus.

The present invention is to provide a pharmaceutical composition comprising bisphosphonate or pharmaceutically acceptable salts thereof as an active ingredient for preventing or treating type II diabetes mellitus.

The present invention is to provide an effective dosage of pharmaceutical composition comprising bisphosphonate or pharmaceutically acceptable salts thereof as an active ingredient for preventing or treating diabetes, more specifically, type II diabetes mellitus.

[Measures to Accomplish the Tasks]

The present invention is to solve the subject by providing a pharmaceutical composition comprising bisphosphonate or pharmaceutically acceptable salts thereof as an active ingredient for preventing or treating diabetes mellitus.

The present invention is to solve the subject by providing a pharmaceutical composition comprising bisphosphonate or pharmaceutically acceptable salts thereof as an active ingredient for preventing or treating type II diabetes mellitus.

The present invention is to solve the subject by providing an effective dosage of pharmaceutical composition comprising bisphosphonate or pharmaceutically acceptable salts thereof as an active ingredient for preventing or treating diabetes, more specifically, type II diabetes mellitus.

Effects of the Invention

The bisphosphonates of the invention can be used as an agent for preventing or treating diabetes mellitus, more specifically type II diabetes mellitus (FIG. 1) by the activities of inhibiting the binding of protein tyrosin phosphatase 1B (PTP-1B) with insulin receptor(IR), and improving insulin secretion from pancreas cells. While it was reported to show severe side effects when administering the dosage of zoledronate, generally 5 mg once a month, for treating bone metastasis in breast cancer, it is expected that the side effects of bisphosphonates to treat diabetes may be neglected since a minimal administering dosage following to the present invention will be effective to treat diabetes.

DESCRIPTION OF THE PREFERRED EMBODIMENTS

Figure 1:
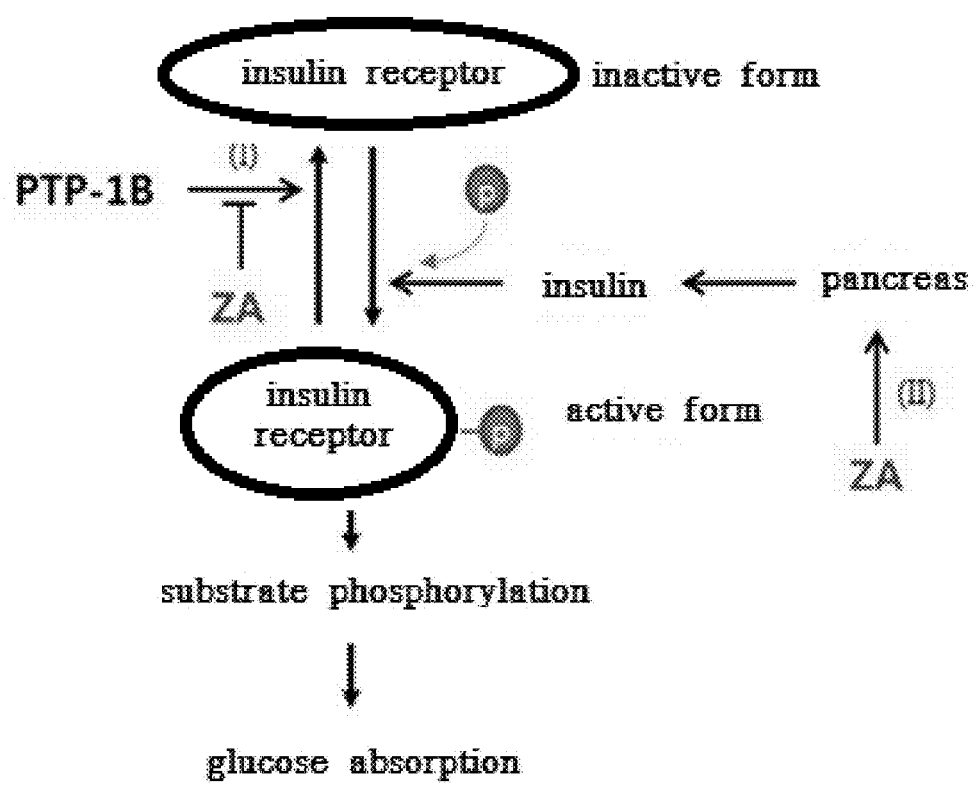
FIG. 1 depicts the inhibition mechanism of PTP-1B insulin signal transduction by zoledronate.

The present invention relates to a pharmaceutical composition comprising bisphosphonate or pharmaceutically acceptable salts thereof as an active ingredient for preventing or treating diabetes mellitus.

More detailed explanation on the present invention follows:

The present invention provides a pharmaceutical composition comprising bisphosphonate compounds as an active ingredient for preventing or treating diabetes.

In one embodiment of the invention, the diabetes mellitus may be type II diabetes mellitus.

The term, "bisphosphonate" and "bisphosphonates," as used herein in referring to the therapeutic agents of the invention are meant to also encompass diphosphonates, biphosphonic acids, and diphosphonic acids, as well as salts and derivatives of these meterials. The use of a specific nomenclature in referring to the bisphosphonate or bisphosphonates is not meant to limit the scope of the present invention, unless specifically indicated.

The bisphosphonates to achieve the purpose of the invention is a compound represented in formula I as follow or its pharmaceutically acceptable salts.

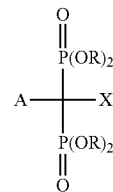

[Formula I]

wherein,

X is hydrogen, hydroxyl, amino, halogen, alkanoyl, or an amino group substituted by $C_{1-4}$ alkyl, or alkanoyl;

R is hydrogen or $C_1$-$C_4$ alkyl and

A is a side chain which contains an optionally substituted amino group, or a nitrogen containing heterocycle (including aromatic nitrogen-containing heterocycles), and pharmaceutically acceptable salts thereof.

Non-limiting examples of bisphosphonates useful herein include the following:

zoledronate([1-hydroxy-2-(1H-imidazol-1-yl)ethane-1,1-diyl]bis(phosphonic acid));

ibandronate({1-hydroxy-3-[methyl(pentyl)amino]propane-1,1-diyl}bis(phosphonic acid));

clodronate((dichloro-phosphono-methyl)phosphonic acid);

etidronate((1-hydroxyethan-1,1-diyl)bis(phosphonic acid));

risedronate((1-hydroxy-1-phosphono-2-pyridin-3-yl-ethyl) phosphonic acid);

tiludronate({[(4-chlorophenyl)thio]methylene}bis(phosphonic acid));

pamidronate((3-amino-1-hydroxypropane-1,1-diyl)bis (phosphonic acid));

alendronate(sodium [4-amino-1-hydroxy-1-(hydroxy-oxido-phosphoryl)-butyl]phosphonic acid trihydrate) and its sodium salt and its calcium salt. The most preferred N-bisphosphonate for use in the invention is 2-(imidazol-lyl)-1-hydroxyethane-1,1-diphosphonic acid (zoledronic acid) or a pharmacologically acceptable salt thereof.

The examples of bisphosphonate, but not limited to, and their structures follow:

[Table 1] examples of bisphosphonates

| name | structure |
|---|---|
| zoledronate | 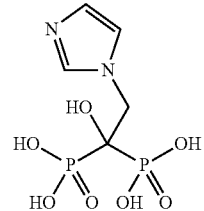 [SMILES: O=P(O)(O)C(O)(Cn1ccnc1)P(=O)(O)O] |

| name | structure |
|---|---|
| ibandronate | (structure) |
| clodronate | (structure) |
| etidronate | (structure) |
| risedronate | (structure) |
| tiludronate | (structure) |
| pamidronate | (structure) |
| alendronate | (structure) |

Especially preferred pharmaceutically acceptable salts are those where one, two, three or four, in particular one or two, of the acidic hydrogens of the bisphosphonic acid are replaced by a pharmaceutically acceptable cation, in particular sodium, potassium or ammonium, in first instance sodium. A preferred group of pharmaceutically acceptable salts is characterized by having one acidic hydrogen and one pharmaceutically acceptable cation, especially sodium, in each of the phosphonic acid groups.

The bisphosphonates maybe used in the form of an isomer or of a mixture of isomers where appropriate, typically as optical isomers such as enantiomers or diastereoisomers or geometric isomers, typically cis-trans isomers. The optical isomers are obtained in the form of the pure antipodes and/or as racemates. The bisphosphonates can also be used in the form of their hydrates or include other solvents used for their crystallisation.

The composition of invention is administered into a patient as a pharmaceutically (therapeutically) effective doasage. Normally the dosage is such that a single dose of the bisphosphonate or its pharmaceutically acceptable salt active ingredient from 0.01-2 mg/day, especially 0.01-1 mg/day, more especially 0.01-0.5 mg/day is administered to a warm-blooded animal weighing approximately 75 kg for preventing or treating diabetes mellitus. If desired, this dose may also be taken in several, optionally equal, partial doses.

The dosage of the bisphosphonate for use in the invention may depend on various factors, such as effectiveness and duration of action of the active ingredient, mode of administration, warm-blooded species, and/or sex, age, weight and individual condition of the warm-blooded animal.

The pharmaceutically acceptable compositions of the invention can be administered to the subject in any conventional administration routes as long as it can be reached to the target tissues. The composition may be, for example, compositions for enteral, such as oral, rectal, aerosol inhalation or nasal administration, compositions for parenteral, such as intravenous or subcutaneous administration, intrapulmonary administration or compositions for transdermal administration. Also, the above composition can be administered by using any device that can be moved to the target cells. The pharmaceutical compositions are adapted to oral or intravenous, parenteral (especially intravenous, intra-arterial or transdermal) administration, but it is not limited thereto.

Pharmaceutical preparations for enteral and parenteral administration are, for example, those in dosage unit forms, such as dragees, tablets or capsules and also ampoules. They are prepared in a manner known per se, for example by means of conventional mixing, granulating, confectioning, dissolving or lyophilising processes. For example, pharmaceutical preparations for oral administration can be obtained by combining the active ingredient with solid carriers, where appropriate granulating a resulting mixture, and processing the mixture or granulate, if desired or necessary after the addition of suitable adjuncts, into tablets or dragee cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, crosslinked polyvinylpyrrolidone, agar or alginic acid or a salt thereof, such as sodium alginate. Adjuncts are especially flow-regulating agents and lubricants, for example silicic acid, talc, stearic acid or salts thereof, such as magnesium or calcium stearate, and/or polyethylene glycol.

Dragee cores are provided with suitable coatings that may be resistant to gastric juices, there being used, inter alia, concentrated sugar solutions that optionally contain gum arabic, talc, polyvinylpyrrolidone, polyethylene glycol and/or titanium dioxide, or lacquer solutions in suitable organic solvents or solvent mixtures or, to produce coatings that are resistant to gastric juices, solutions of suitable cellulose preparations, such as acetylcellulose phthalate or hydroxypropylmethylcellulose phthalate. Colouring substances or pigments may be added to the tablets or dragee coatings, for example for the purpose of identification or to indicate different doses of active ingredient.

Other orally administrable pharmaceutical preparations are dry-filled capsules made of gelatin, and also soft, sealed capsules made of gelatin and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, where appropriate, stabilisers. In soft capsules the active ingredient is preferably dissolved or suspended in suitable liquids, such as fatty oils, paraffin oil or liquid polyethylene glycols, it being possible also for stabilisers to be added.

Parenteral formulations are especially injectable fluids that are effective in various manners, such as intravenously, intraarterially, intramuscularly, intraperitoneally, intranasally, intradermally, subcutaneously, preferably intravenously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilized and/or contain adjuncts, for example preservatives, stabilizers, wetting agents and/or emulsifiers, solubilizers, salts for regulating the osmotic pressure and/or buffers.

As used herein, the term "subject" (or patient) refers to all animals including humans which have disease or have the possibility to develop diabetes mellitus to be prevented or treated. The above disease may be effectively prevented or treated by administering the composition comprising the compound of the invention to the subject.

As used herein, "treatment" or "treating," is used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight, gender and age of the subject, the severity of the disease condition, the manner of administration, formulation of the product, health condition, and the like, which can readily be determined by one of ordinary skill in the art. The specific dose will vary depending on the particular compounds chosen, the dosing regimen to be followed, whether it is administered in combination with other compounds, timing of administration, the tissue to which it is administered, and the physical delivery system in which it is carried. In case of standardized to 70 Kg man, general dosage may be 0.1 mg to 1,000 mg/day, preferably 1 to 500 mg/day, more preferably 10 to 100 mg/day and the daily dosage may be administered once or divided over a few times per day at a decision made by a doctor or a pharmacist.

The pharmaceutical composition of the invention may be administered to a patient independently or in a combination therapy with the other therapeutic agents for treating metabolic bone diseases. The composition may be administered to a patient simultaneously or separately with the other therapeutic agents. Also, the composition may be administered in single or multiple. Considering all the above stated factors, it is important to administer adequate dosage to get the maximum effect by the least amount of the compound with minimal side effect and the dosage may be determined easily by those skilled in the art.

The term "co-administration," "administered in combination with," and their grammatical equivalents, as used herein, encompass administration of two or more agents to an animal so that both agents and/or their salts are present in the animal at the same time. Co-administration includes simultaneous administration in separate compositions, administration at different times in separate compositions, or administration in a composition in which both agents are present.

In one embodiment of the invention, the bisphosphonate or its pharmaceutically acceptable salt inhibits the binding of protein tyrosin phosphatase 1B(PTP-1B) with insulin receptor(IR), and improves insulin releasing from pancreas cells of subject with diabetes mellitus.

In one embodiment of the invention, the bisphosphonate or its pharmaceutically acceptable salt may be administered with other agent in combination therapy or co-administrative therapy. Thus, the invention may comprise a method of treatment for diabetes mellitus including combination therapy or co-administration of bisphosphonate or its pharmaceutically acceptable salt with other agents for treating diabetes mellitus.

EXPERIMENTAL EXAMPLE 1

Inhibition of Binding PTP-1B with IR By Zoledronate

IR molecules stood for 1 hour at 30° C. to induce phosphorylation, and each 1 µl of IR molecules were fixed with protein chips(PeproTech) at 4° C. The protein chips were washed with washing buffer for 10 minutes, and blocked with blocking buffer(3% BSA in PBS, pH 7.4) at room temperature for 1 hour followed by washing with washing buffer. Each sample was as follow:

0. Blank control(C), 0.5 µl PEG (10%, polyethylene glycol)+0.5 µl PTP-1B buffer;
1. Negative control(N), 0.5 µl PEG (10%)+0.5 µl PTP-1B;
2. Positive control(P), 0.5 µl $Na_3VO_4$(sodium orthovanadate; 1 mM, pH 10)+0.5 µl PTP-1B;
3. Experimental group(ZA), 0.5 µl ZA (5 µM)+0.5 µl PTP-1B The protein chips were washed for 10 minutes, and each was treated with 1 µl of anti-IR phosphorylation antibodies diluted by dilution buffer in 1/100 followed by incubating for 1 hour at 30° C. And then, it was washed with washing buffer for 10 minutes, and each was treated with 1 it of Cy5-fluorescent coupled rabbit anti-IgG antibodies diluted by dilution buffer in 1/100 followed by incubating for 1 hour at 30° C. They were washed for 10 minutes, scanned by microarray scanner system to analyze to GraphPad Prism 4 software.

The results are presented as the mean±SD(%). Statistical analysis was performed using Student's t-test, and P<0.05 was considered as a significance (n=6).

Figure 2:
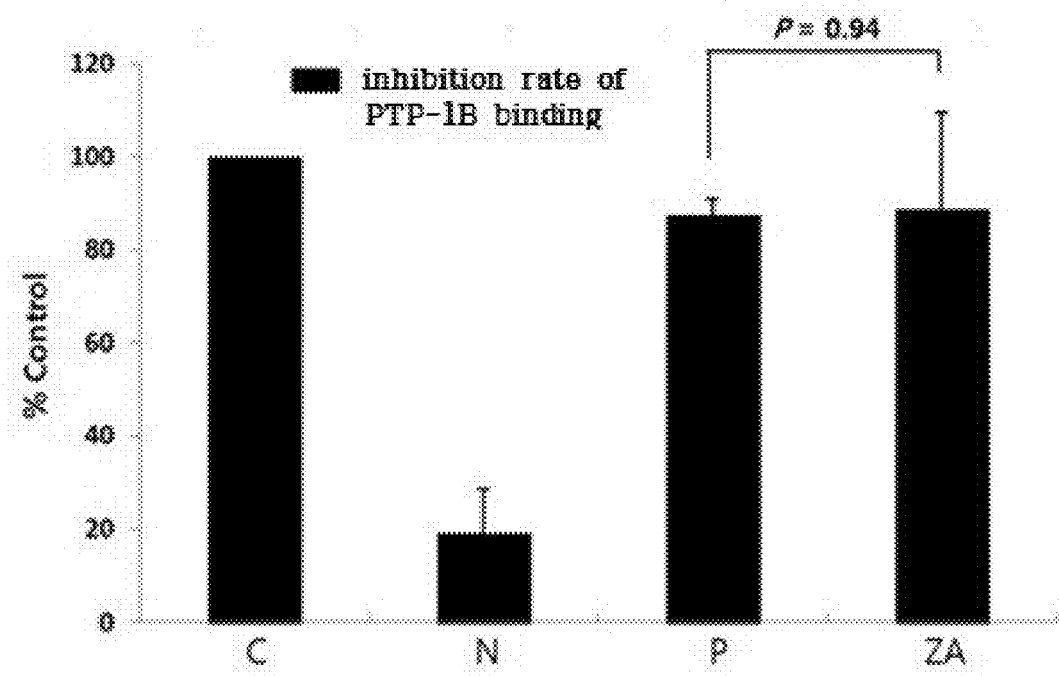
FIG. 2 depicts the inhibitory effect on the binding of insulin receptor with PTP-1B when administering zoledronate.

In the positive control, $Na_3VO_4$ was used as a PTP-1B inhibitor (i.e., compound that inhibits dephosphorylation of IR protein by phosphatase, PTP-1B). The inhibition effect of binding PTP-1B with IR in negative control was 19±10%, whereas in positive control, it was 87±4%. In ZA, it was 89±21% and the inhibition effect by treating ZA was similar with positive control or more superior than positive control (FIG. 2)

EXPERIMENTAL EXAMPLE 2

Analysis of Insulin Secretion Level by Hyperglycemia Stimulation

Rat pancreatic islets were isolated from Sprague Dawley rats (200~230 g) by digesting the pancreatic duct with collagenase P (1 mg/ml in PBS).

After digestion, the islets were separated with Histopaque-1077 (Sigma, St. Louis, Mo.). The primary islets were cultured in RPMI 1640 medium containing 10% fetal bovine serum (FBS), penicillin (100 IU/ml) and streptomycin (100 g/ml).

Equal number of primary islet clusters was transferred into micro-centrifuge tube with 1 ml of 10% RPMI 1640, and incubated under normal (5.5 mM glucose) and glucotoxic conditions with or without Zoledronic acid (5 μM) for 3 days.

Exposure to glucotoxic conditions was followed by treating with 0.6 mM free fatty acid (FFA; palmitate/oleate, 2:1) and 25 mM glucose in RPMI 1640 with 10% FBS. FFA were complexed with 5% fatty acid-free BSA in PBS.

Cultured islets were washed in Krebs-Ringer-bicarbonate (KRB) buffer (130 mM NaCl, 3.6 mM KCl, 1.5 mM $CaCl_2$, 0.5 mM $MgSO_4$, 0.5 mM $KH_2PO_4$. 2.0 mM $NaHCO_2$ and 10 mM HEPES) and incubated in KRB buffer for 1 hour followed by further incubation in KRB buffer containing 5.5 mM glucose for 1 hour.

Samples were centrifuged at 12,000 g for 1 min and the supernatant was collected for measurement. The pellets were washed in KRB buffer twice, and then stimulated for 1 hour in KRB buffer containing 25 mM glucose. Insulin concentrations from two supernatants removed at two different conditions were measured with a RIA kit (Linco)

The results are presented as the mean±SD of five independent experiments. Statistical analysis was performed using Student's t-test, and $P<0.05$ was considered as a significance.

Figure 3:
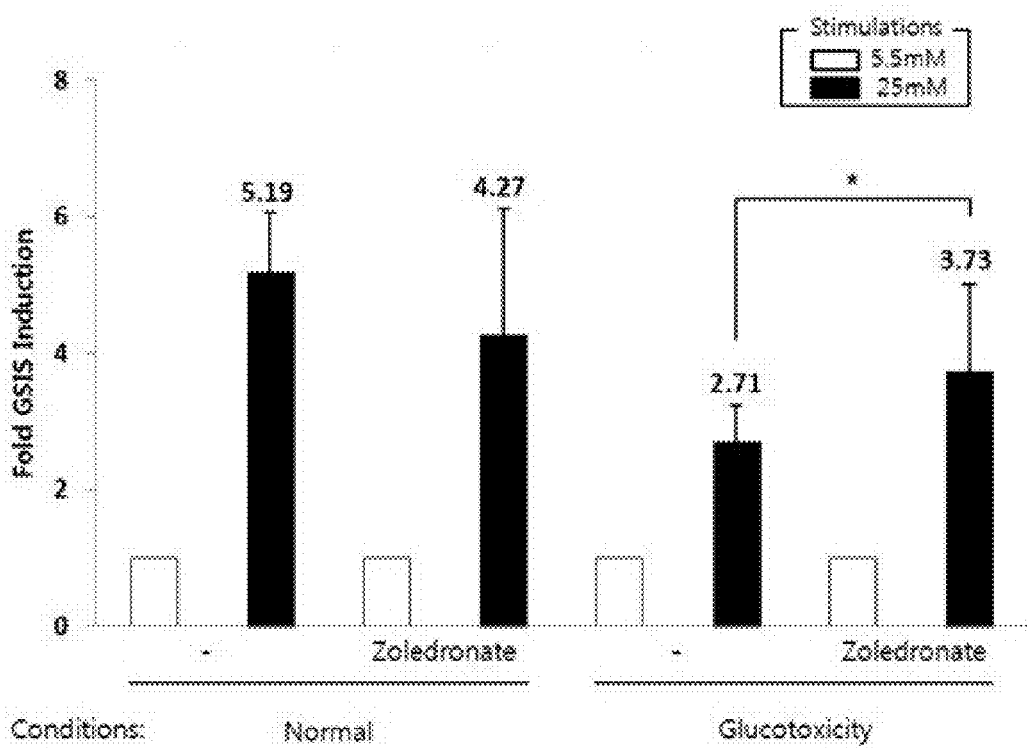
FIG. 3 depicts the stimulatory effect on insulin release in condition of diabetes mellitus when administering zoledronate.

In normal condition(i.e., 5.5 mM glucose), insulin secretion levels were similar with each other, in 5 μM ZA treated group(82±43%) and pancreatic duct (100±17%). However, in diabetes mellitus condition(i.e., 25 mM glucose), insulin secretion level was reduced to 52±19% compared to the normal condition, however it restored to 72±34% (FIG. 3). It seems that more reliable results can be expected when conducting a dose-dependent analysis of ZA.

PREPARATION EXAMPLE 1

The preparation of the powder form
ZA 10 mg
Sucrose 100 mg
Talc 10 mg
The above ingredients were mixed and filled in packs to obtain the powder form.

PREPARATION EXAMPLE 2

The preparation of the tablet form
ZA 10 mg
Starch 100 mg
Sucrose 100 mg
Magnesium Stearate 2 mg The above ingredients were mixed and the mixture was formulated into tablets.

PREPARATION EXAMPLE 3

The preparation of the capsule form
ZA 10 mg
Crystalline Celluose 3 mg
Lactose 15 mg
Magnesium Stearate 1 mg
The above ingredients were mixed and the mixture was formulated into capsules by using gelatin capsule.

PREPARATION EXAMPLE 4

The preparation of the granule form
ZA 10 mg
Soybean extracts 50 mg
Glucose 200 mg
Starch 500 mg
The above ingredients were mixed, 100 mL of 30% ethanol was added and dried in 60° C. to formulate granules.

PREPARATION EXAMPLE 5

The preparation of the pill form.
ZA 20 mg
Lactose 1,500 mg
Glycerin 1,500 mg
Starch 980 mg
The above ingredients were mixed and the mixture was formulated into pills by using conventional methods. The weight of one pill was 4 g.

PREPARATION EXAMPLE 6

The preparation of the injection
ZA 10 mg
Mannitol 180 mg
Sterile distilled water for injection 2,970 mg
$Na_2HPO_4 12H_2O$ 30 mg
The above ingredients were mixed and the mixture was formulated into injection by using conventional methods. The volume of each of the ampules was 2 mL.

PREPARATION EXAMPLE 7

The preparation of the solution.
ZA 10 mg
Isomerized glucose syrup 10,000 mg
Mannitol 5,000 mg
Purified water Properly
The above ingredients were mixed and dissolved into the purified water by using conventional methods. Proper flavoring agent was added to the above mixture and sterilized to formulated into solutions.

What is claimed is:

1. A method of treating diabetes mellitus, the method comprising single or multiple administration of a pharmaceutical composition comprising zoledronate or a pharmaceutically acceptable salt thereof as an active ingredient to a patient in need thereof.

2. The method of treating diabetes mellitus of claim 1, wherein the diabetes mellitus is type II diabetes mellitus.

3. A method of treating diabetes mellitus, the method comprising single or multiple administration of a therapeutically effective dose of a pharmaceutical composition comprising zoledronate or a pharmaceutically acceptable salt thereof as an active ingredient thereof to a patient in need thereof.

4. The method of treating diabetes mellitus of claim 3, wherein the therapeutically effective dose is a range of 0.001 mg to 0.2 mg/day.

5. The method of treating diabetes mellitus of claim 3, wherein the therapeutically effective dose is a range of 0.001 mg to 0.15 mg/day.

6. The method of treating diabetes mellitus of claim 3, wherein the therapeutically effective dose is a range of 0.01 mg to 0.1 mg/day.

* * * * *